United States Patent
Peyser et al.

[11] Patent Number: 5,868,759
[45] Date of Patent: Feb. 9, 1999

[54] SURGICAL CLIP APPLIER

[75] Inventors: Mark S. Peyser, Easton; Csaba L. Rethy, Fairfield, both of Conn.

[73] Assignee: United States Surgical Corporation

[21] Appl. No.: 948,549

[22] Filed: Oct. 10, 1997

[51] Int. Cl.$^6$ .................................................. A61B 17/04
[52] U.S. Cl. ......................... 606/139; 606/142; 227/901
[58] Field of Search ................................... 606/142, 143; 227/901

[56] References Cited

U.S. PATENT DOCUMENTS

| | | |
|---|---|---|
| 2,968,041 | 1/1961 | Skold . |
| 3,152,336 | 10/1964 | Brady . |
| 3,646,801 | 3/1972 | Caroll . |
| 3,753,438 | 8/1973 | Wood et al. . |
| 4,086,926 | 5/1978 | Green et al. . |
| 4,152,920 | 5/1979 | Green . |
| 4,166,466 | 9/1979 | Jarvik . |
| 4,185,762 | 1/1980 | Froehlich . |
| 4,196,836 | 4/1980 | Becht . |
| 4,201,314 | 5/1980 | Samuels et al. . |
| 4,226,242 | 10/1980 | Jarvik . |
| 4,228,895 | 10/1980 | Larkin . |
| 4,242,902 | 1/1981 | Green . |
| 4,246,903 | 1/1981 | Larkin . |
| 4,256,251 | 3/1981 | Moshofsky . |
| 4,296,751 | 10/1981 | Blake, III et al. . |
| 4,299,224 | 11/1981 | Noiles . |
| 4,316,468 | 2/1982 | Klieman et al. . |
| 4,325,376 | 4/1982 | Klieman et al. . |
| 4,372,316 | 2/1983 | Blake, III et al. . |
| 4,408,603 | 10/1983 | Blake, III et al. . |
| 4,410,125 | 10/1983 | Noiles et al. . |
| 4,412,539 | 11/1983 | Jarvik . |
| 4,425,915 | 1/1984 | Ivanov . |
| 4,427,008 | 1/1984 | Transue . |
| 4,430,997 | 2/1984 | DiGiovanni et al. . |
| 4,448,193 | 5/1984 | Ivanov . |
| 4,450,839 | 5/1984 | Transue . |
| 4,450,840 | 5/1984 | Mericle et al. . |
| 4,452,357 | 6/1984 | Klieman et al. . |
| 4,452,376 | 6/1984 | Klieman et al. . |
| 4,471,780 | 9/1984 | Menges et al. . |
| 4,478,218 | 10/1984 | Mericle . |
| 4,478,220 | 10/1984 | DiGiovanni et al. . |

(List continued on next page.)

FOREIGN PATENT DOCUMENTS

| | | |
|---|---|---|
| 0068046 | 1/1983 | European Pat. Off. . |
| 0406724 | 1/1991 | European Pat. Off. . |
| 0409569 | 1/1991 | European Pat. Off. . |
| 0507537 | 10/1992 | European Pat. Off. . |
| 0612505 | 8/1994 | European Pat. Off. . |
| 0623316 | 11/1994 | European Pat. Off. . |
| 8202825 | 9/1982 | WIPO . |
| 8801486 | 3/1988 | WIPO . |
| 9003763 | 4/1990 | WIPO . |
| 9421181 | 9/1994 | WIPO . |

OTHER PUBLICATIONS

Ethicon, "Ligaclip: Ligating Clips & Appliers", 1982.
Reynolds, Jr., "Metal Clip Techniques Utilizing Pistol Grip Appliers", *American Journal of Surgery*, vol. 143, Feb. 1982.
U.S. Surgical Corporation, Information Booklet for Auto Suture® Premium Surgiclip™ Titanium Disposable Automatic Clip Appliers.
Weck, "We've Corrected Everybody's Flaws. Even Our Own.", *Surgery: Gynecology & Obsetrics*, vol. 163, No. 3, Sep. 1986.
Weck, "Deep Surgery Advantage: New Access Plus Automatic-Feed In Vessel Ligation".

*Primary Examiner*—Gary Jackson

[57] ABSTRACT

A surgical clip applier includes a housing, a pair of handles pivotably connected to opposite sides of the housing, a channel assembly extending from the housing and a jaw assembly. A pusher bar assembly is provided to feed clips from a series of clips to the jaw mechanism under the influence of a spring, and a damping mechanism is provided to generate a force on the pusher member to counteract the spring force and decelerate the distal advancement of the pusher member as a clip is fed to the jaw assembly.

16 Claims, 14 Drawing Sheets

U.S. PATENT DOCUMENTS

| | | |
|---|---|---|
| 4,480,640 | 11/1984 | Becht . |
| 4,480,641 | 11/1984 | Failla et al. . |
| 4,492,232 | 1/1985 | Green . |
| 4,500,024 | 2/1985 | DiGiovanni et al. . |
| 4,509,518 | 4/1985 | McGarry et al. . |
| 4,512,345 | 4/1985 | Green . |
| 4,522,207 | 6/1985 | Klieman et al. . |
| 4,532,925 | 8/1985 | Blake, III . |
| 4,534,351 | 8/1985 | Rothfuss et al. . |
| 4,549,544 | 10/1985 | Favaron . |
| 4,556,058 | 12/1985 | Green . |
| 4,557,263 | 12/1985 | Green . |
| 4,562,839 | 1/1986 | Blake, III et al. . |
| 4,565,199 | 1/1986 | Becht . |
| 4,572,183 | 2/1986 | Juska . |
| 4,576,166 | 3/1986 | Montgomery et al. . |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,637,395 | 1/1987 | Caspar et al. . |
| 4,646,740 | 3/1987 | Peters et al. . |
| 4,662,373 | 5/1987 | Montgomery et al. . |
| 4,662,374 | 5/1987 | Blake, III . |
| 4,674,504 | 6/1987 | Klieman et al. . |
| 4,691,853 | 9/1987 | Storace . |
| 4,712,549 | 12/1987 | Peters et al. . |
| 4,850,355 | 7/1989 | Brooks et al. . |
| 4,967,949 | 11/1990 | Sandhaus . |
| 5,030,226 | 7/1991 | Green et al. . |
| 5,047,038 | 9/1991 | Peters et al. . |
| 5,049,152 | 9/1991 | Simon et al. . |
| 5,067,958 | 11/1991 | Sandhaus . |
| 5,084,057 | 1/1992 | Green et al. . |
| 5,100,420 | 3/1992 | Green et al. . |
| 5,104,395 | 4/1992 | Thornton et al. . |
| 5,112,343 | 5/1992 | Thornton . |
| 5,156,609 | 10/1992 | Nakao et al. . |
| 5,171,247 | 12/1992 | Hughett et al. . |
| 5,171,249 | 12/1992 | Stefanchik et al. . |
| 5,192,288 | 3/1993 | Thompson et al. . |
| 5,207,692 | 5/1993 | Kraus et al. . |
| 5,211,649 | 5/1993 | Kohler et al. . |
| 5,246,450 | 9/1993 | Thornton et al. . |
| 5,330,487 | 7/1994 | Thornton et al. . |
| 5,403,327 | 4/1995 | Thornton et al. . |
| 5,409,498 | 4/1995 | Braddock et al. . |
| 5,431,668 | 7/1995 | Burbank, III et al. . |
| 5,700,270 | 12/1997 | Peyser et al. .......................... 606/142 |

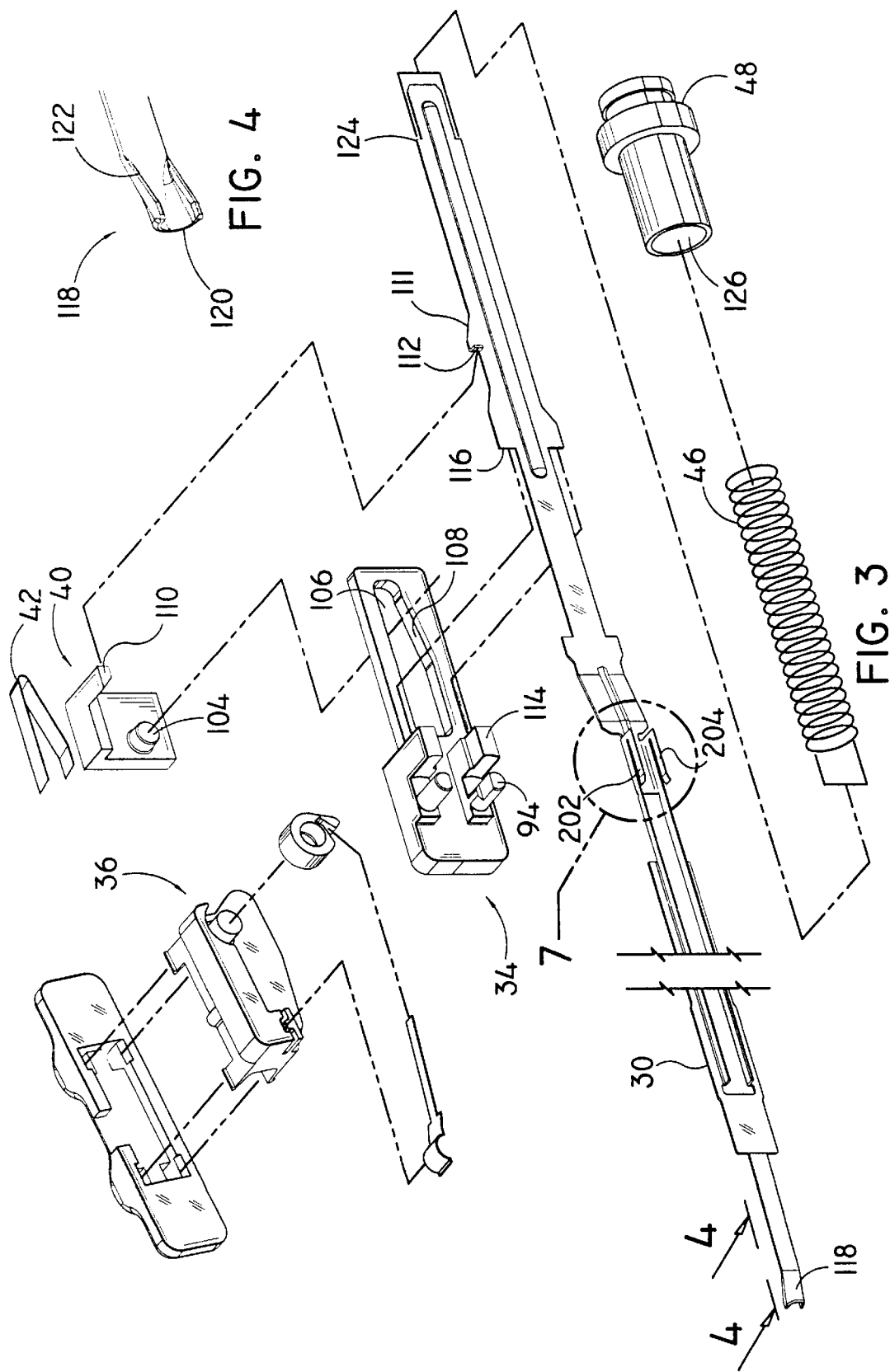

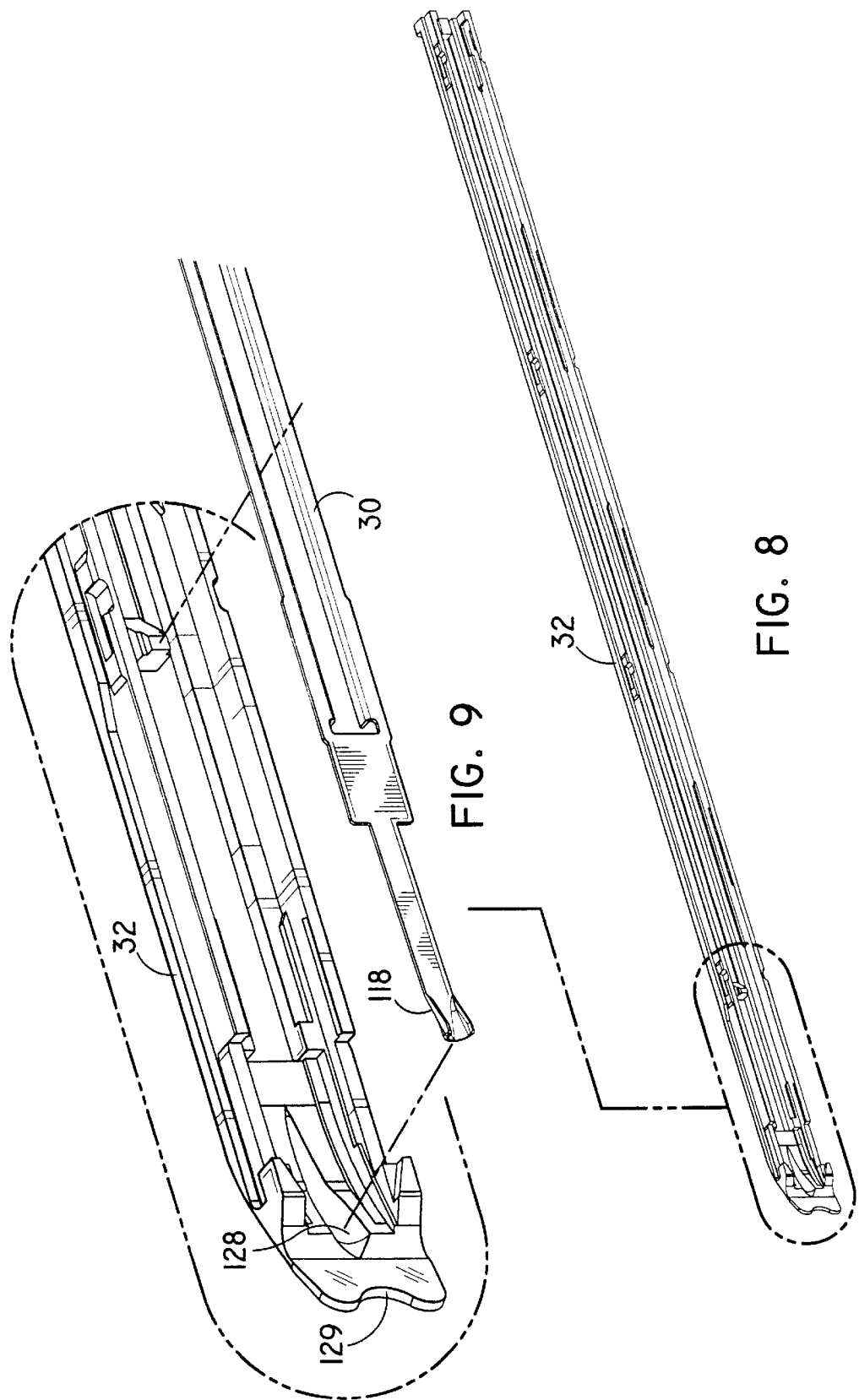

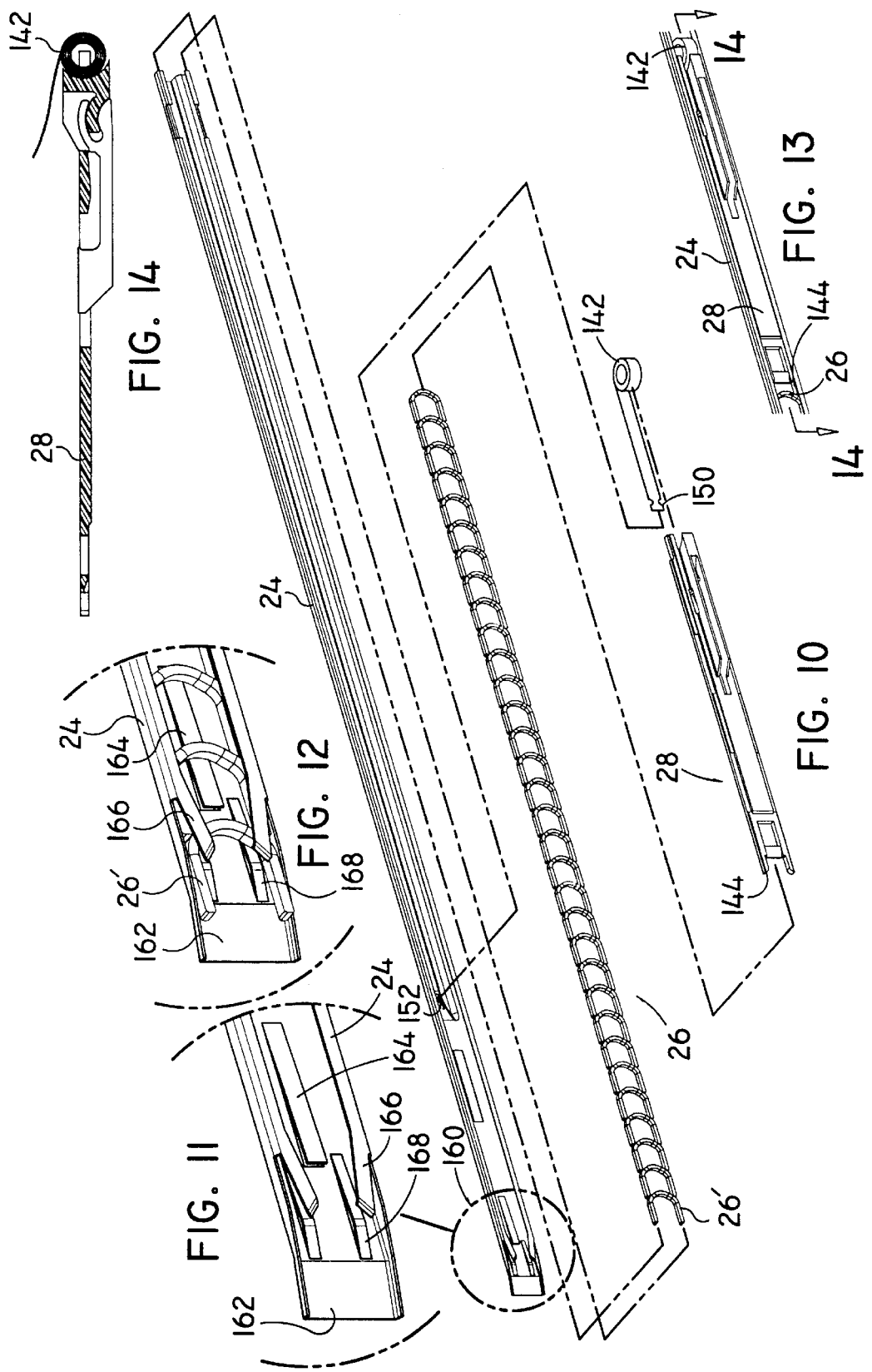

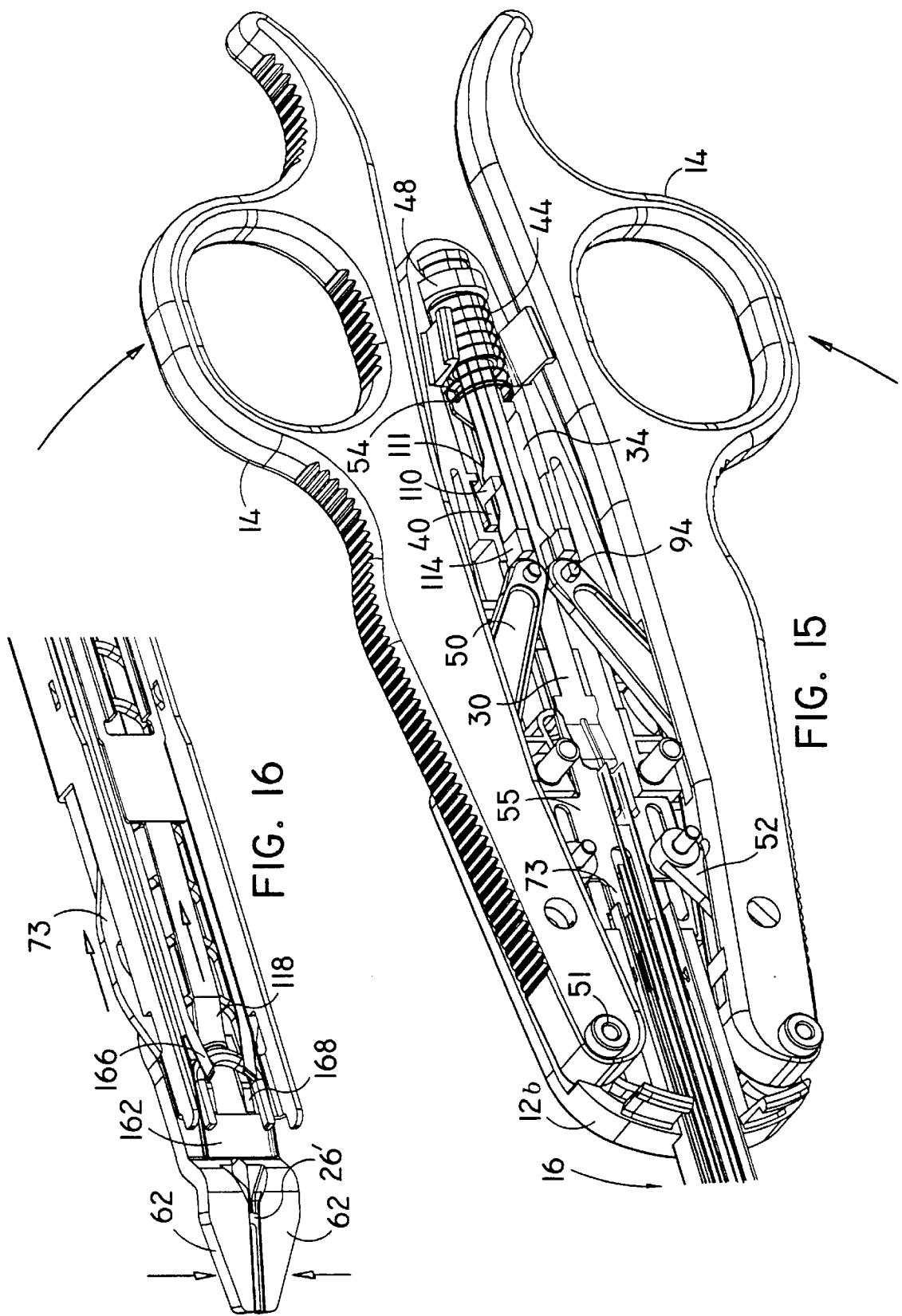

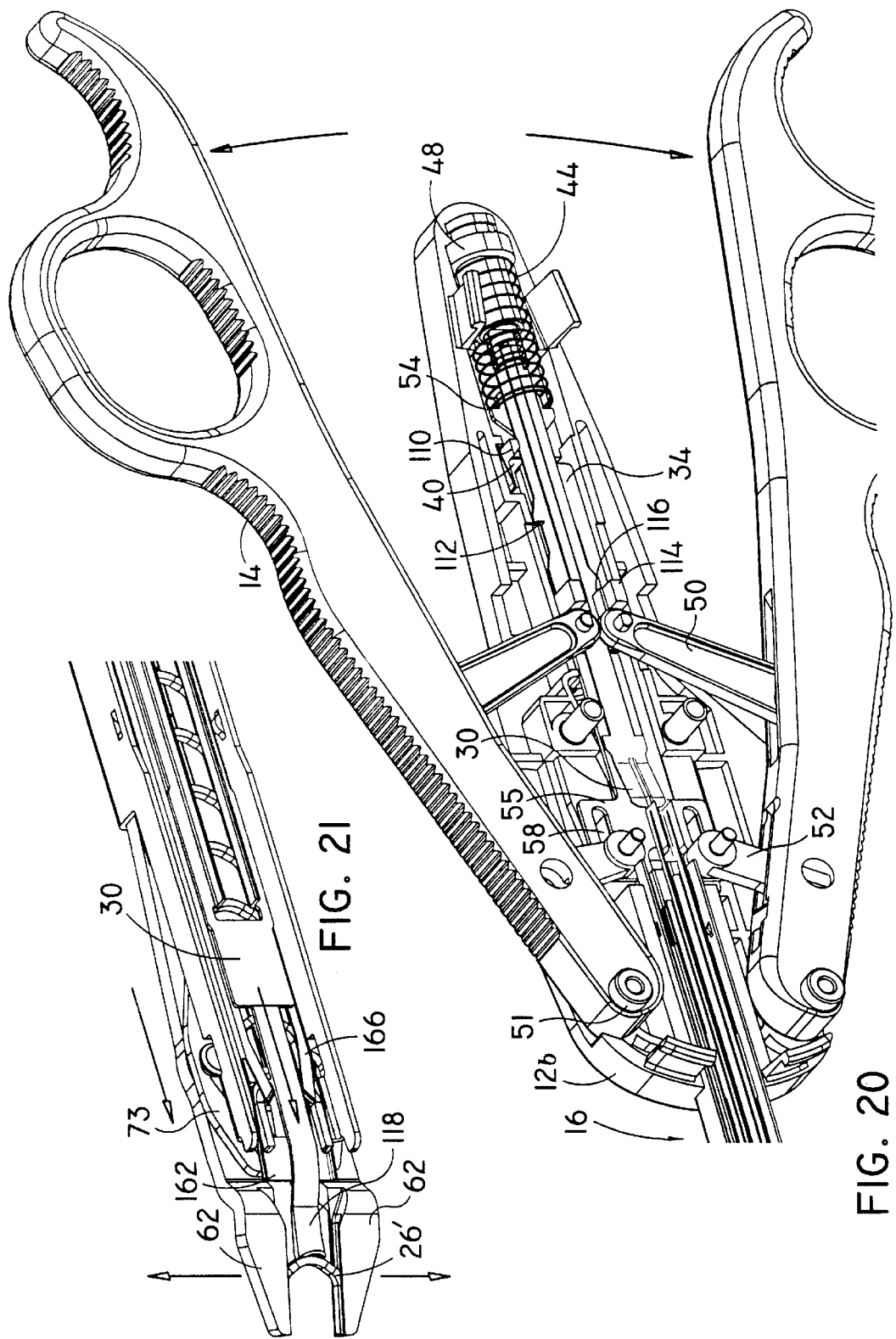

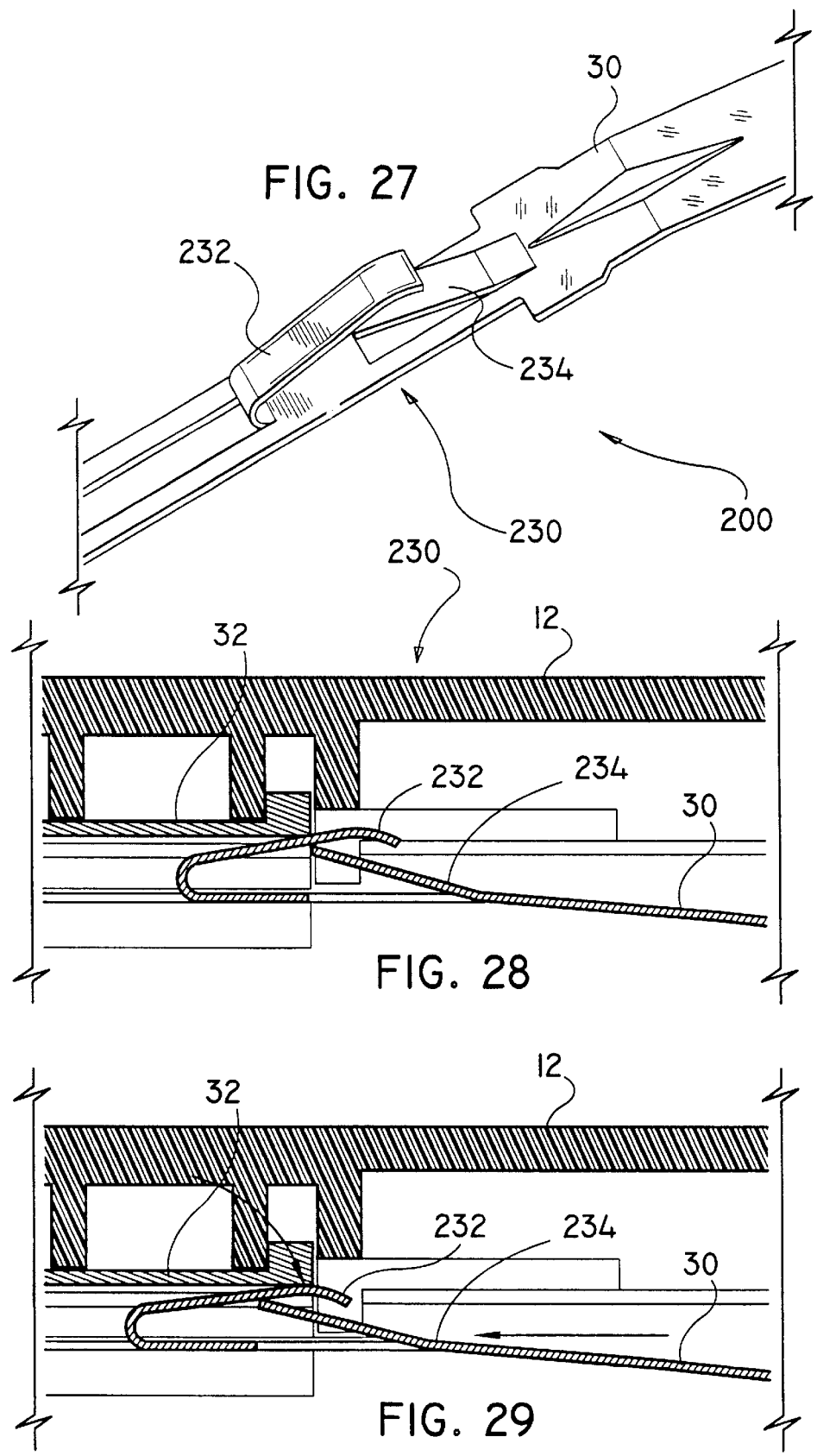

SURGICAL CLIP APPLIER

BACKGROUND

1. Technical Field

The present application relates to surgical clip appliers, and in particular relates to instruments having a plurality of clips for applying the clips to body tissues and vessels during surgical procedures.

2. Discussion of the Prior Art

Surgical clip appliers are known in the art and have increased in popularity among surgeons by offering an alternative to conventional suturing of body tissues and vessels. Typical instruments are disclosed in U.S. Pat. No. 5,030,226 to Green et al. and U.S. Pat. No. 5,431,668 to Burbank, III et al. These instruments generally provide a plurality of clips which are stored in the instrument and which are fed sequentially to the jaw mechanism at the distal end of the instrument upon opening and closing of the handles at the proximal end of the instrument. As the handles are closed, the jaws close to deform a clip positioned between the jaw members, and as the jaws are opened to release the deformed clip, a new clip is fed from the series to a position between the jaws. This process is repeated until all the clips in the series of clips have been used.

In addition, many of the prior art instruments provide complex mechanical arrangements for closing the jaws while simultaneously preparing for feeding the next clip into the jaws after the clip positioned between the jaws is deformed and then released. These complex mechanisms, such as that shown in U.S. Pat. No. 5,431,668 to Burbank, III et al., require numerous parts which increases the cost of manufacture, as well as increasing the time it takes to assemble each instrument. These arrangements typically require additional moving parts, also tending to increase the cost of manufacture and increase the time of assembly.

Furthermore, many prior art instruments provide a clip feed mechanism in which the clip feed bar, or clip pusher bar is spring biased into a "load" position, and then is released and driven with considerable force and speed to drive a clip into the jaw mechanism. The forward movement of the clip is often arrested by either a clip stop mechanism at the jaws, by friction within the jaws, or by a combination of friction and the abrupt termination of the feed stroke of the pusher bar itself. A disadvantage of mechanisms of this type is that due to the force of the feed stroke, many times the clip itself may be inaccurately placed in the jaws, or may actually be overfed to the jaws, resulting in the clip becoming dislodged prior to application, or being otherwise inaccurately placed during application.

A need therefore exists for an instrument which controls the clip feeding procedure from the clip carrier to the jaws, so that the disadvantages of the prior art are overcome in that the possibility of misfeeding the clips to the jaws is substantially reduced or effectively eliminated. A need also exists for an instrument having a clip feed mechanism which reduces the force of the clip feed mechanism during the feed stroke to accurately place the clip into the jaws without misaligning the clip with respect to the jaws.

SUMMARY

A surgical clip applier is disclosed which is both highly efficient and reliable, and which reduces the number of parts which make up the instrument to provide a low cost, easy to assemble instrument. The instrument provides a reliable clip feed mechanism which reduces or effectively eliminates misfeeding and/or inaccurate placement of clips in the jaw mechanism.

The surgical clip applier includes a housing at a proximal end of the instrument, with at least one handle pivotably attached to the housing on opposite sides of the instrument. In a preferred embodiment, a channel assembly or body portion may extend from the housing and may be fixedly secured thereto. The channel assembly terminates in a jaw assembly which includes a pair of jaw members which may be fixedly secured to the distal end of the channel assembly. In this embodiment, neither the channel nor the jaws move during opening and closing of the handles with respect to a longitudinal axis of the instrument, as defined by the channel assembly, although in other embodiments either or both may move.

The handles are secured to the housing at a pivot point, and further include a pair of links connecting each handle to the movable components positioned within the housing. A first link connects each handle to a cam plate which is slidably positioned in the channel assembly and which is operably connected to the jaw members for opening and closing the jaw members as the handles open and close. A second link is provided on each handle and is connected to a drive plate which controls the movement of a clip pusher bar, which itself is slidably positioned within the channel assembly and terminates adjacent the jaw members. Also positioned within the channel assembly is a plurality of clips arranged in series relation on a clip carrier. The series of clips is urged distally towards the jaw members by a clip follower which is biased in the distal direction by a constant force spring.

It is desirable for the clip applier to have a clip initially stored between the jaw members so that the clip applier is ready to use after it is removed from its package. Alternately, the instrument may be packaged with the handles already in the closed position, so that as the instrument is removed from the package, the handles open to advance a clip to the jaws, as described below, and the instrument is ready to use. As the jaws are positioned about tissue, or about a hollow vessel such as a body duct or blood vessel, the surgeon squeezes the handles to move the handles from the open position to the closed position. As this occurs in the preferred embodiment, the first link on the handles causes the jaw members to close to deform the clip positioned between the jaws.

As the handles are closed, the second link on the handles serves to move the clip pusher bar in a proximal direction against the biasing of a pusher bar spring. At the distal end of the instrument, the nose portion of the pusher bar is moved into position behind the distalmost clip in the series of clips and is ready to feed the next clip to the jaws. As the pusher bar is moved in the proximal direction, upon completion of the closing stroke of the handles, the pusher bar may be latched by a spring biased latch member in the housing so that the nose portion is held in position behind the distalmost clip.

As the handles are released, the jaws open, thus releasing the is deformed clip from between the jaws. The pusher bar may be held against forward movement for a delay period until the handles and jaws are substantially opened, at which time the latch is released and the pusher bar is moved in a distal direction under the influence of the biasing spring. As the pusher bar moves in the distal direction, the nose portion of the pusher bar feeds the distalmost clip from the series of clips into the jaw members.

In order to properly align the clip in the jaw members, and to reduce the possibility of a misfeed due to the considerable force generated by the biasing spring, the present device includes a damping or braking mechanism which slows the forward advancement of the pusher bar so that the clip is advanced in a controlled, steadily decreasing force which allows the clip to slide gently into the jaw members. The novel damping or braking mechanism thus substantially reduces the possibility of a misfeed occurring during the clip feeding procedure.

BRIEF DESCRIPTION OF THE DRAWINGS

The present clip applier will be more fully appreciated as the same becomes better understood from the following detailed description when considered in connection with the following drawings, in which:

FIG. 3 illustrates an exploded perspective of the clip pusher bar subassembly;

FIG. 4 illustrates an enlarged perspective view of the nose portion of the pusher bar taken along lines 4—4 of FIG. 3;

FIGS. 8 and 9 illustrate a perspective view of the channel cover with respect to the pusher bar member;

FIG. 10 illustrates an exploded perspective view of the clip carrier subassembly which includes the series of clips and the clip follower;

FIGS. 11 and 12 illustrate an enlarged perspective view of the distal end of the clip carrier showing the clip carrier with and without clips loaded thereon, respectively;

FIG. 13 illustrates a partial perspective view of the clip carrier subassembly showing the clip follower in position behind the series of clips;

FIG. 14 illustrates a side cross-sectional view of the clip follower taken along lines 14—14 of FIG. 13;

FIG. 15 illustrates a perspective view of the handle of the clip applier, with the top cover removed, showing the position of the components in the housing as the handles are closed;

FIG. 16 illustrates a perspective view of the distal end of the instrument with the channel cover removed, showing the position of the jaws corresponding to the position of the handles as shown in FIG. 15;

FIG. 20 illustrates a perspective view of the handle of the clip applier, with the top cover removed, showing the position of the components in the housing when the handles are in the fully opened position;

FIG. 21 illustrates a perspective view of the distal end of the instrument with the channel cover removed, showing the position of the jaws when the handles are in the position shown in FIG. 20;

FIG. 27 illustrates another embodiment of the damping or braking mechanism; and

FIGS. 28 and 29 illustrate the braking mechanism of FIG. 27 in use.

DETAILED DESCRIPTION OF THE PREFERRED EMBODIMENT

Figure 1:
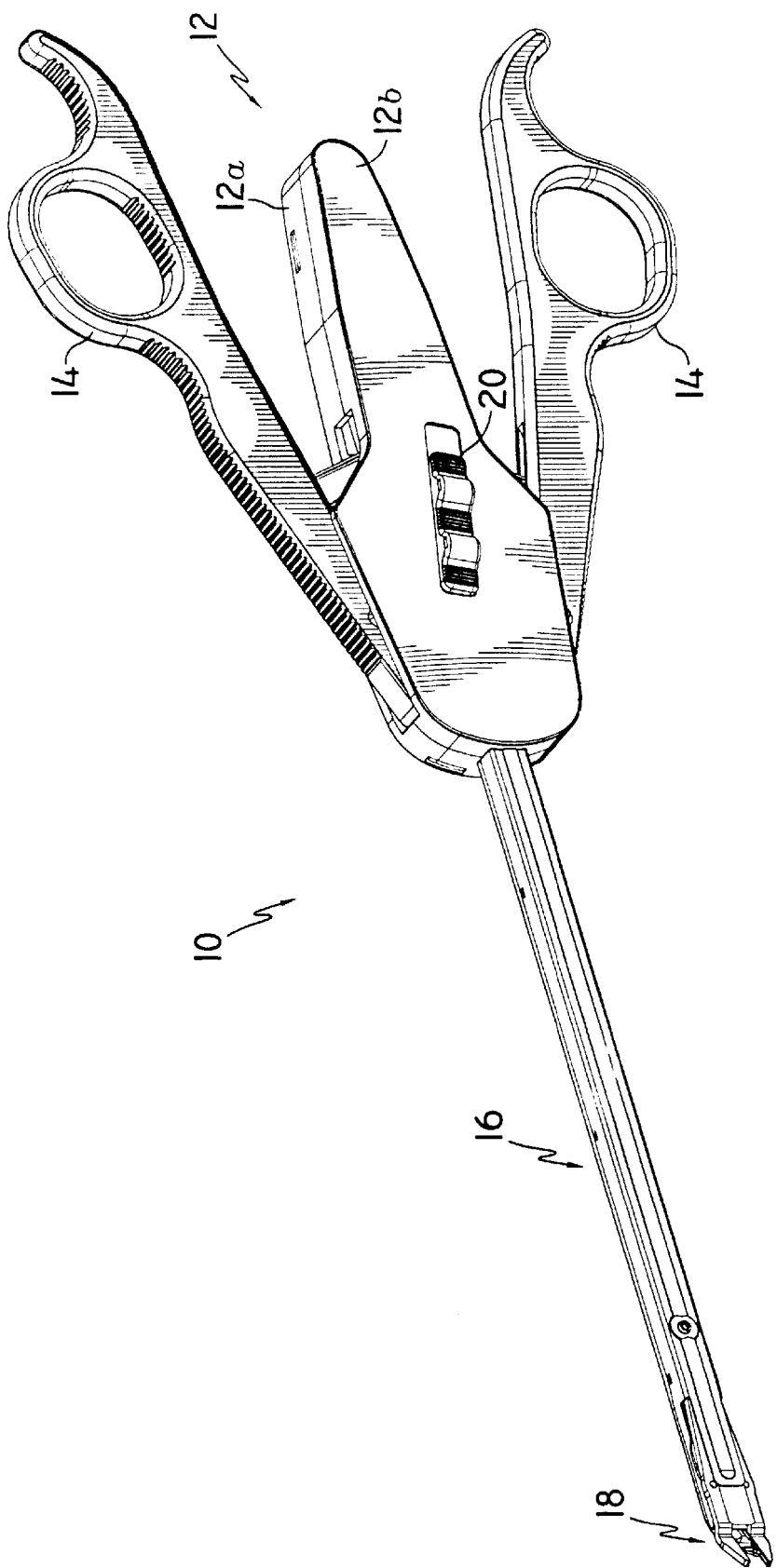
FIG. 1 illustrates a perspective view of the clip applier.

Referring now to the drawings, in which like reference numerals identify similar or identical elements throughout the several views, and referring in particular to FIGS. 1 and 2, a surgical clip applier 10 having the novel damping mechanism as described hereinbelow includes a housing 12 having an upper housing half 12a and lower housing half 12b. A pair of handles 14 are pivotably secured to the housing 12 and extend outwardly therefrom. A channel assembly 16 extends outwardly from the housing 12, terminating in a jaw assembly 18. A ratchet button 20 may be provided if desired to provide for incremental closure of the jaws.

Figure 2:
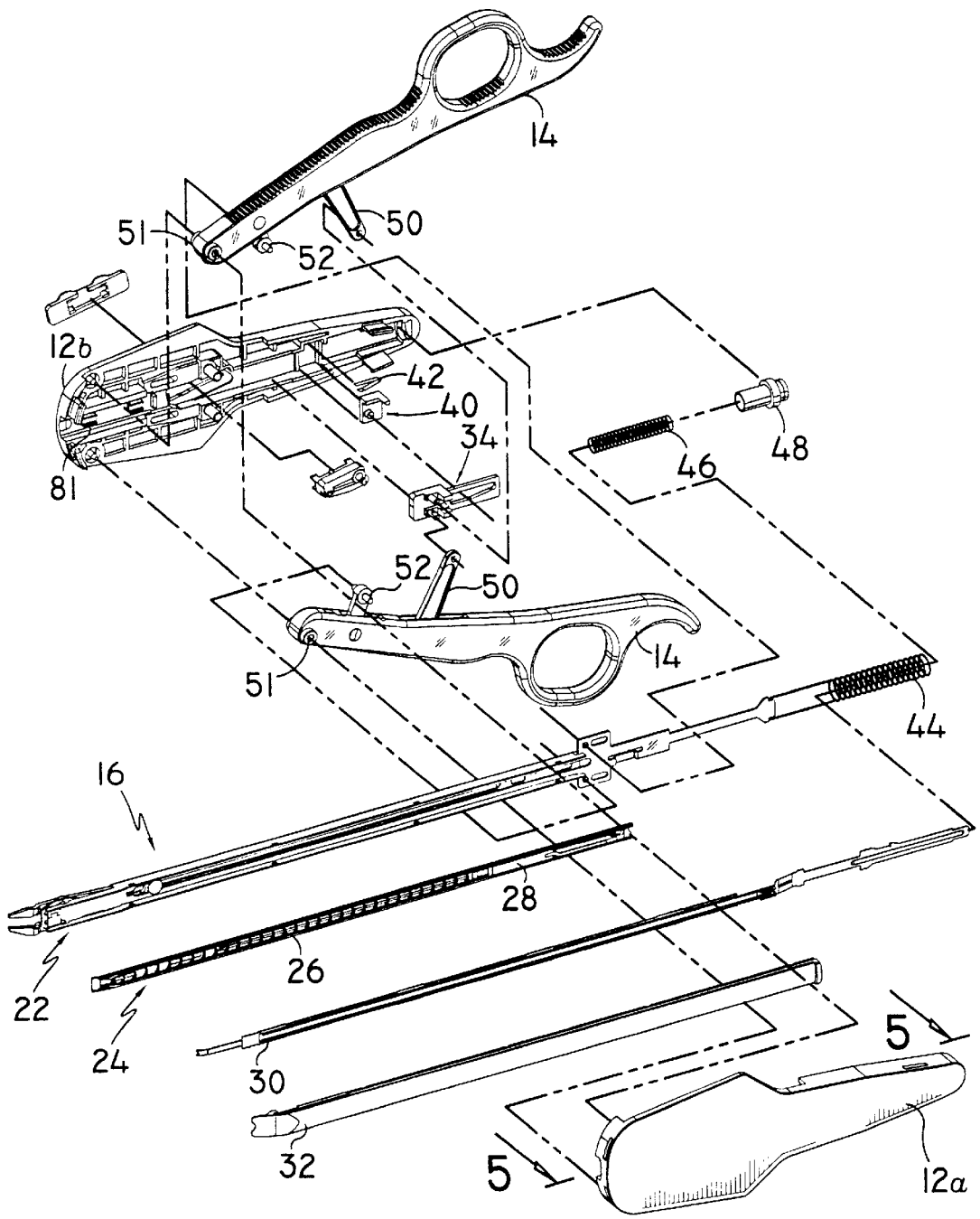
FIG. 2 illustrates an exploded perspective view of the clip applier.

Referring now to FIG. 2, there is illustrated an exploded perspective view of clip applier 10 which shows the components of the instrument. Housing halves 12a and 12b preferably fit together by snap fit although any suitable method for securing the housing halves together in a conventional manner is acceptable. Channel assembly 16 includes channel subassembly 22, and clip carrier 24 which includes a plurality of clips 26 which are urged towards the jaw assembly 18 by clip follower 28. Clip pusher bar 30 is also positioned in channel assembly 16 and is enclosed within the channel assembly 16 by channel cover 32. In one embodiment, the channel assembly 16 is fixedly secured to housing 12 so that it does not move upon closure of the handles, although in an alternate embodiment the channel assembly may be movable to assist in closure of the jaw members as is known.

Also positioned within housing 12, is drive plate 34 which controls movement of the clip pusher bar 30. Drive plate 34 cooperates with latch plate 40 and latch spring 42 to control the movement of pusher bar 30 in a distal direction for feeding clips to the jaw assembly. Cam plate spring 44 and pusher bar spring 46 are assembled with spring sleeve 48 to bias the cam plate and pusher bar, respectively in a distal direction. Handles 14 are secured to housing 12 by handle pivot posts 51. A pair of link members 50 and 52 are provided, where pusher bar link 50 is connected to drive plate 34 to control the movement of pusher bar 30, while cam plate link 52 is secured to cam plate 73 to control the movement of the cam plate 73.

Referring now to FIGS. 3 and 4, there is illustrated the pusher bar member 30 and the mechanism which effects movement of pusher bar member 30. Pusher bar member 30 terminates at its distal end in nose portion 118, which as shown in FIG. 4, includes nose engaging surface 120 which engages the clips to be fed to the jaw mechanism, and ramped portion 122. The distal end can be of any suitable configuration. FIGS. 8 and 9 show the position of nose portion 118 with respect to the distal end of channel cover 32, where nose portion 118 fits within a nose portion groove 128 adjacent the tissue stop 129 of channel cover 32.

As seen in FIG. 3, drive plate 34 includes pusher bar link post members 94 to which are secured pusher bar links 50 of handles 14. Drive plate 34 also includes driving abutment surface 114 which engages pusher bar drive tab 116, and further includes latch cam slot 106 which accommodates latch post 104 of latch plate 40. Latch post 104 cooperates with cam surface 108 of latch cam slot 106 to release pusher bar 30 to feed a clip to the jaw mechanism as will be described below. Latch plate 40 also includes latching bar 110 which engages latch tab 112 of pusher bar 30 as will be described below.

The proximal end of pusher bar 30 includes spring abutment surface 124 which engages pusher bar spring 46 which is fit in the cavity 126 of spring sleeve 48. Spring 46 biases pusher bar 30 in a distal direction towards the jaw assembly. Also shown in FIG. 3 is a ratchet mechanism 36 which may be provided to permit incremental closure of the jaw members.

Figure 5:
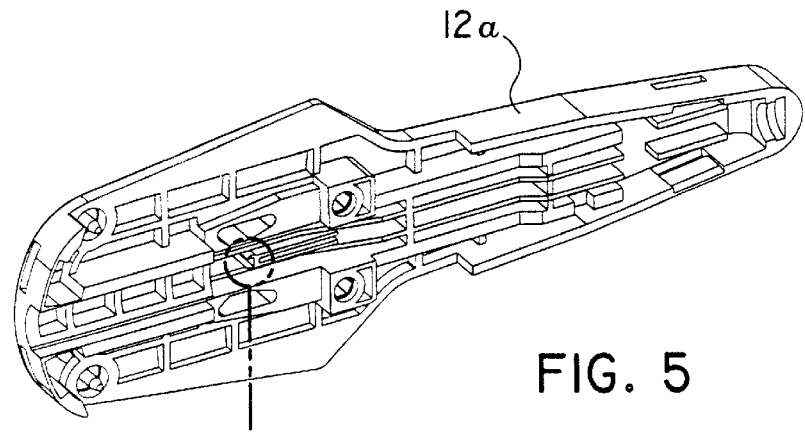
FIG. 5 illustrates the inner housing wall showing the location of the cam surfaces of the braking or damping mechanism according to a first embodiment.
Figure 6:
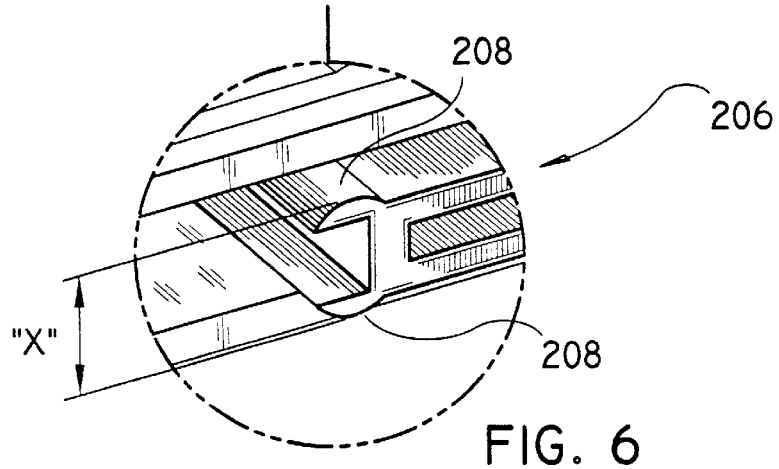
FIG. 6 illustrates an enlarged view of the cam surfaces of FIG. 5.
Figure 7:
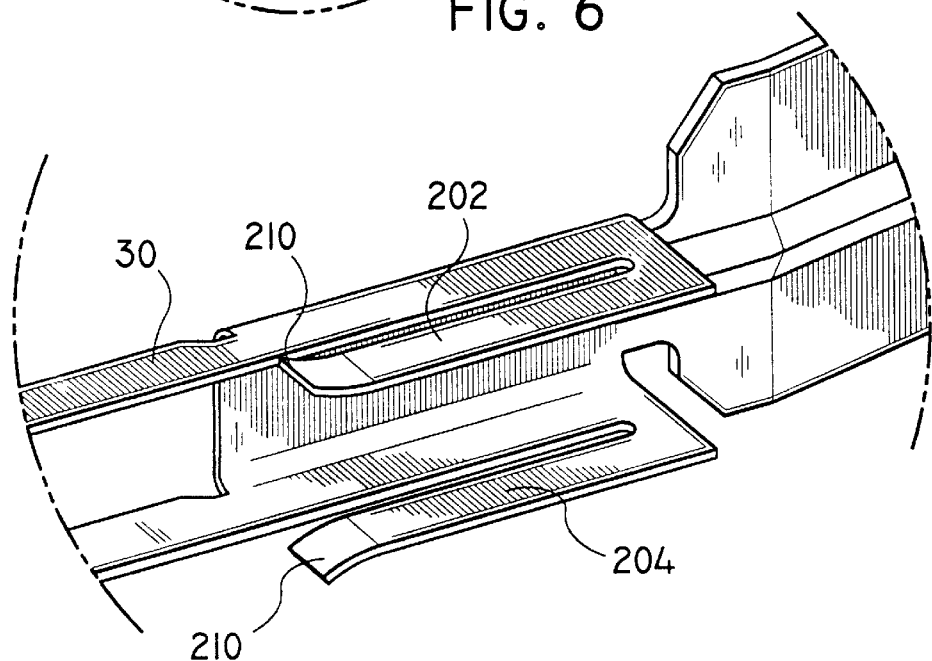
FIG. 7 illustrates an enlarged view of the section of FIG. 3 showing the spring members of the pusher bar which cooperate with the cam surfaces to comprise the braking or damping mechanism.

Pusher bar 30 also includes the spring members 202, 204 of damping mechanism 200, which is best seen in FIGS. 5–7. Damping mechanism 200 shows the distal acceleration of pusher bar 30 after latch 40 is disengaged to release the pusher bar to feed a clip to the jaws. Damping mechanism 200 substantially reduces or eliminates misfeeding or misalignment of the clip at jaw assembly 18. Damping mechanism 200 includes cam boss 206 which is constructed on the inside wall of housing half 12a, preferably during molding of housing half 12a. Cam boss 206 includes cam surfaces 208, which curve outwardly as shown. Damping mechanism 200 further includes spring members 202, 204 of pusher bar 30, which have flared ends 210 as shown. Spring members 202, 204 ride over and frictionally engage cam surfaces 208, and serve to decelerate the advancement of pusher bar 30 during a feed stroke of pusher bar 30. During advancement, flared ends 210 engage cam surfaces 208, and are deflected outwardly. Friction between the spring members 202, 204 and cam surfaces 208 decelerates the speed of advancement of pusher bar 30. The distance between spring members 202 and 204 is less than the distance X (defined by the outer surfaces of cam surfaces 208).

Turning now to FIGS. 10–14, there is illustrated the clip carrier subassembly which includes clip carrier 24 upon which is positioned a series of clips 26 which are urged in the distal direction by clip follower 28. Clip follower 28 also includes clip engaging posts 144, which engage the proximalmost clip in the series of clips as seen in FIG. 13 to urge the entire series of clips towards the clip exit portion 160 of clip carrier 24. Clip follower 28 is urged in the distal direction by constant force spring 142 which is secured at feed spring tab 150 to feed spring catch 152 on clip carrier 24, as seen in FIG. 10. When the series of clips is present on clip carrier 24, constant force spring 142 is unrolled, to provide the biasing force on the series of clips. As the clips are dispensed, spring 142 coils or rolls up on itself, to move clip follower 28 in the distal direction and urge the clips towards the jaw mechanism.

As illustrated in FIGS. 11 and 12, the series of clips are held in place by the combination of clip holding lance 166 which provides a downward force on the spring, and clip holding lance 168 which provides an upward force on the spring. Clip stop 164 prevents rearward movement of the distalmost clip 26'. As will be described below, clip ramp 162 is at the distal end of clip carrier 24.

The operation of clip applier 10 having the damping mechanism 200 will now be described, with particular reference to FIGS. 15–22. Instrument 10 can be packaged with a clip 26 disposed between the jaw members 62 so that the instrument is ready to use immediately or can be packaged with the handles in the closed position, so that as the instrument is removed from the package, the handles move to the open position to feed a clip to the jaws to place the instrument into a "ready" condition. To close a clip, as seen in FIG. 15, handles 14 are moved from the open position to the closed position as shown, which causes a clip 26' to be deformed between the jaw members 62 as shown in FIG. 16. As the handles close, links 50 and 52 are moved in the proximal direction as shown.

As handles 14 are closed, links 52, whose pivot pins are positioned in pivot pin holes 56 of flared portion 55 of cam plate 73 move the cam plate in the proximal direction against the biasing of spring 44 which is moved to a compressed state by spring abutment surface 54. Once handles 14, and consequently cam plate 73 is moved to the position shown in FIGS. 15 and 16, the jaw members 62 are moved to the position shown in FIG. 16 to deform a clip 26' positioned therebetween. This occurs by moving cam plate 73 in a proximal direction so that the jaws are moved towards each other.

As handles 14 are moved to the position shown in FIG. 15, links 50, which are secured to drive plate 34 at pusher bar link post 94 move drive plate 34 in the proximal direction to the position shown in FIG. 15. As this occurs, the driving abutment surface 114 of drive plate 34 engages drive tab 116 of pusher bar 30 to drive pusher bar 30 in the proximal direction against the biasing of pusher spring 46. As this occurs, latch plate 40, which is biased downwardly by latch spring 42, rides along the edge of pusher bar 30 as pusher bar 30 moves in the proximal direction. Latch locking bar 110 rides on the ramped surface 111 until the ramped surface 111 clears the latch locking bar 110 so that latch locking bar 110 is positioned against pusher bar latch tab 112 as shown in FIG. 15. Pusher bar 30 is therefore latched into the position shown in FIG. 15.

Referring to FIG. 16, it can be seen that the pusher bar 30 has moved proximally so that nose portion 118 is positioned behind the next clip in the series, which is held on clip carrier 24 by clip holding lances 166 and 168 as described above.

Figure 17:
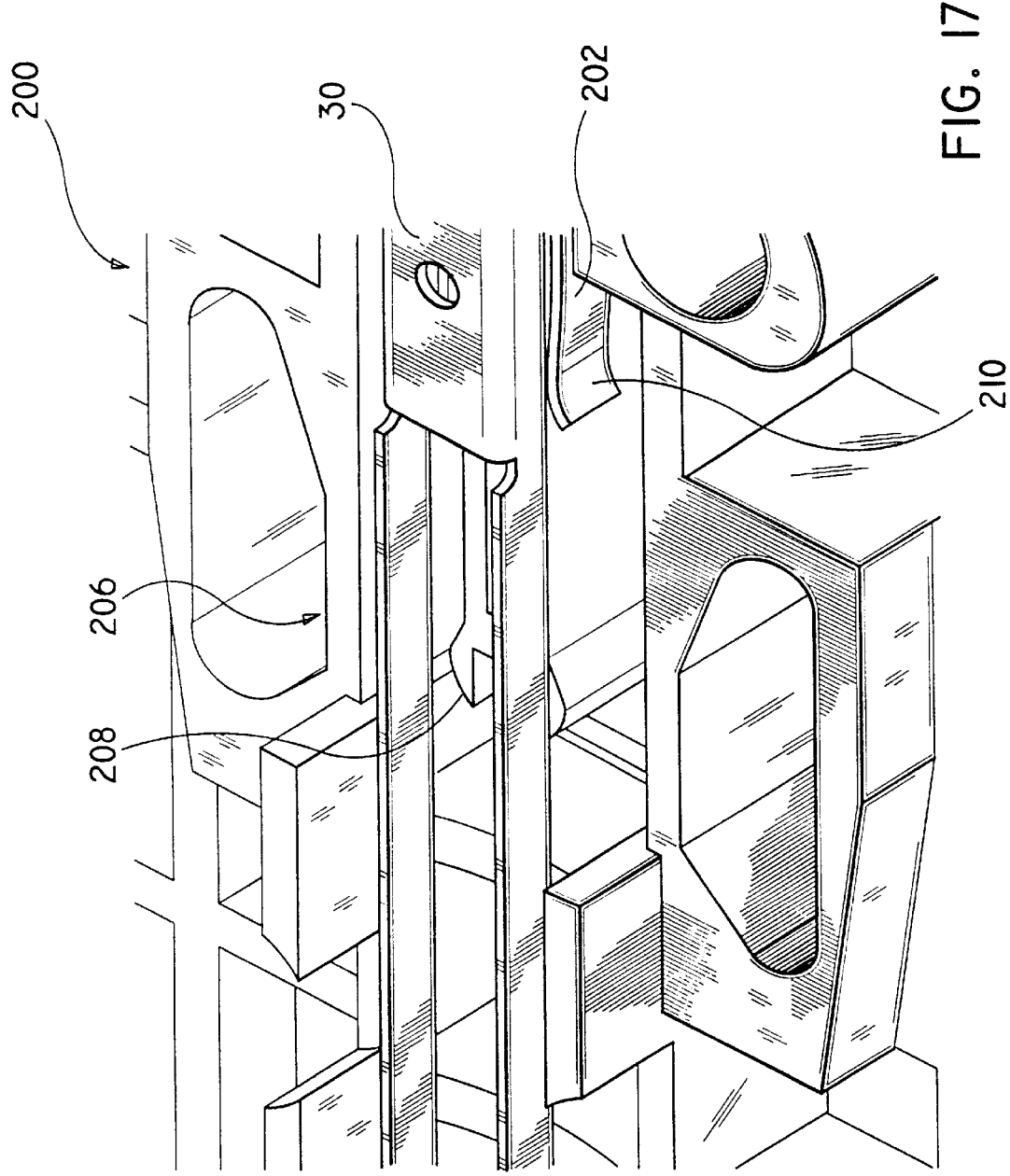
FIG. 17 illustrates the cam surfaces and spring members of the damping mechanism of FIGS. 5–7 when the pusher bar is in the position of FIG. 15.

With reference to FIG. 17, when the pusher bar 30 is in the position shown in FIGS. 15 and 16, the damping mechanism 200 moved to the position shown in FIG. 17. Damping mechanism 200 is moved proximally with the pusher bar 30 so that spring members 202 and 204 are proximal of cam boss 206 (and cam surfaces 208).

Figures 18, 19:
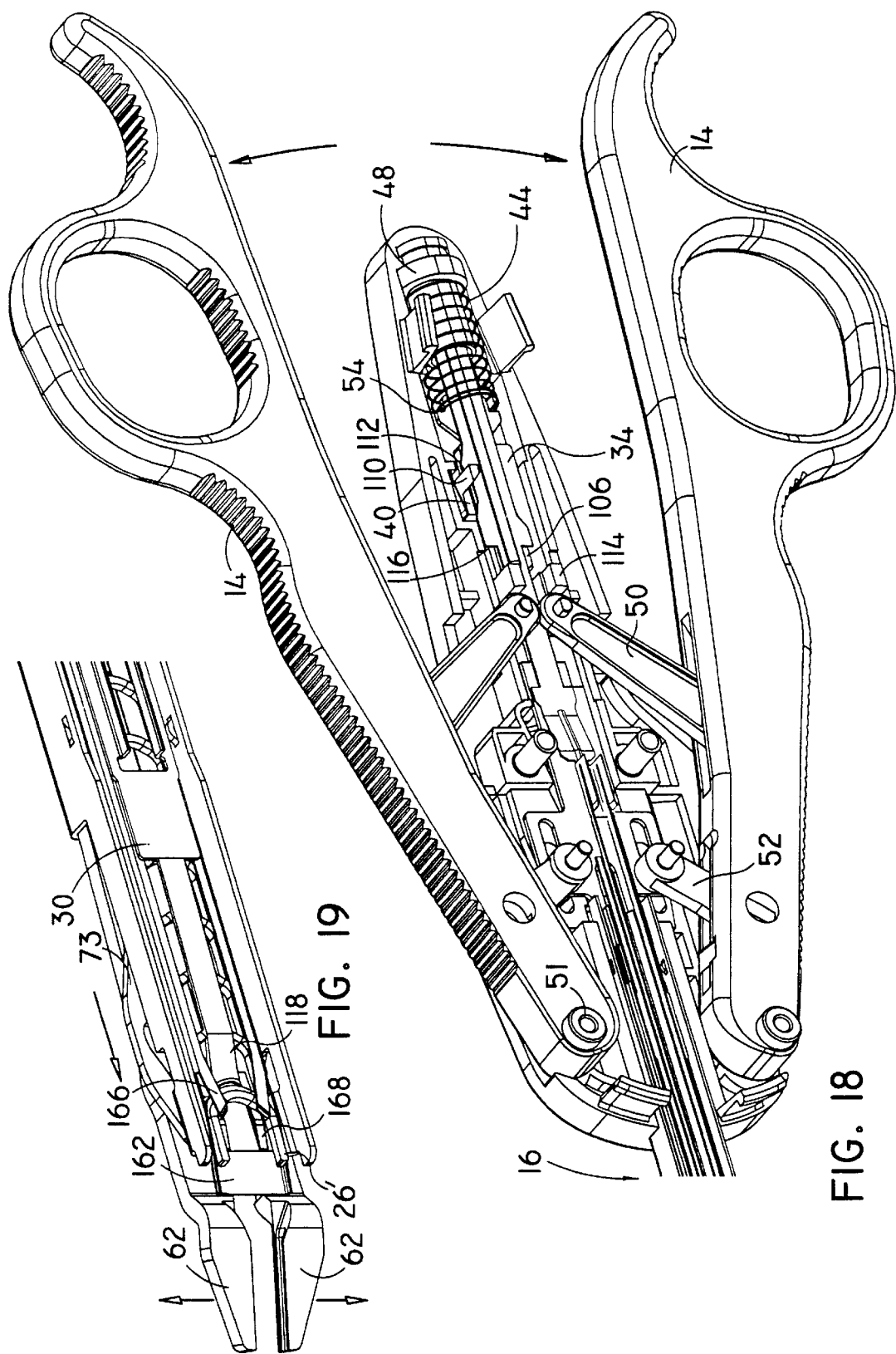
FIG. 18 is a perspective view of the handle of the clip applier, with the top cover removed, showing the position of the components in the housing as the handles are in the opening stroke.
FIG. 19 illustrates a perspective view of the distal end of the instrument with the channel cover removed, showing the position of the jaws corresponding to the position of the handles as shown in FIG. 18.

As the handles are released, they begin to move from the closed position to the open position under the bias of spring 44, as shown in FIGS. 18 and 19. Links 50 and 52 begin to move drive plate 34 and cam plate 73, respectively, in the distal direction towards the jaw mechanism. As seen in FIG. 19, jaw members 62 begin to open as cam plate 73 slides in the distal direction, and as the handles continue to open, drive plate 34 moves with links 50 in the distal direction as the handles are opened under the influence of spring 44. However, as can be seen in FIG. 18, pusher bar 30 remains latched at pusher bar latch tab 112 as it is engaged by latch locking bar 110 of latch plate 40. Driving abutment surface 114 of drive plate 34 moves away from drive tab 116 of pusher bar 30.

Drive plate 34, as stated above, includes latch cam slot 106 which accommodates latch post 104 of latch plate 40 (see FIG. 9). As drive plate 34 moves in the distal direction, post 104 rides in slot 106 until post 104 engages cam surface 108 of latch cam slot 106. As this occurs, and as will be described with reference to FIG. 20, the ramped surface of cam slot 108 causes post 104 to ride up the ramped surface against the biasing of spring 42. FIG. 19 shows the nose portion 118 of pusher bar 30 in position behind the distalmost clip 26' of the series of clips ready to be fed into the jaw members 62.

Figure 22:
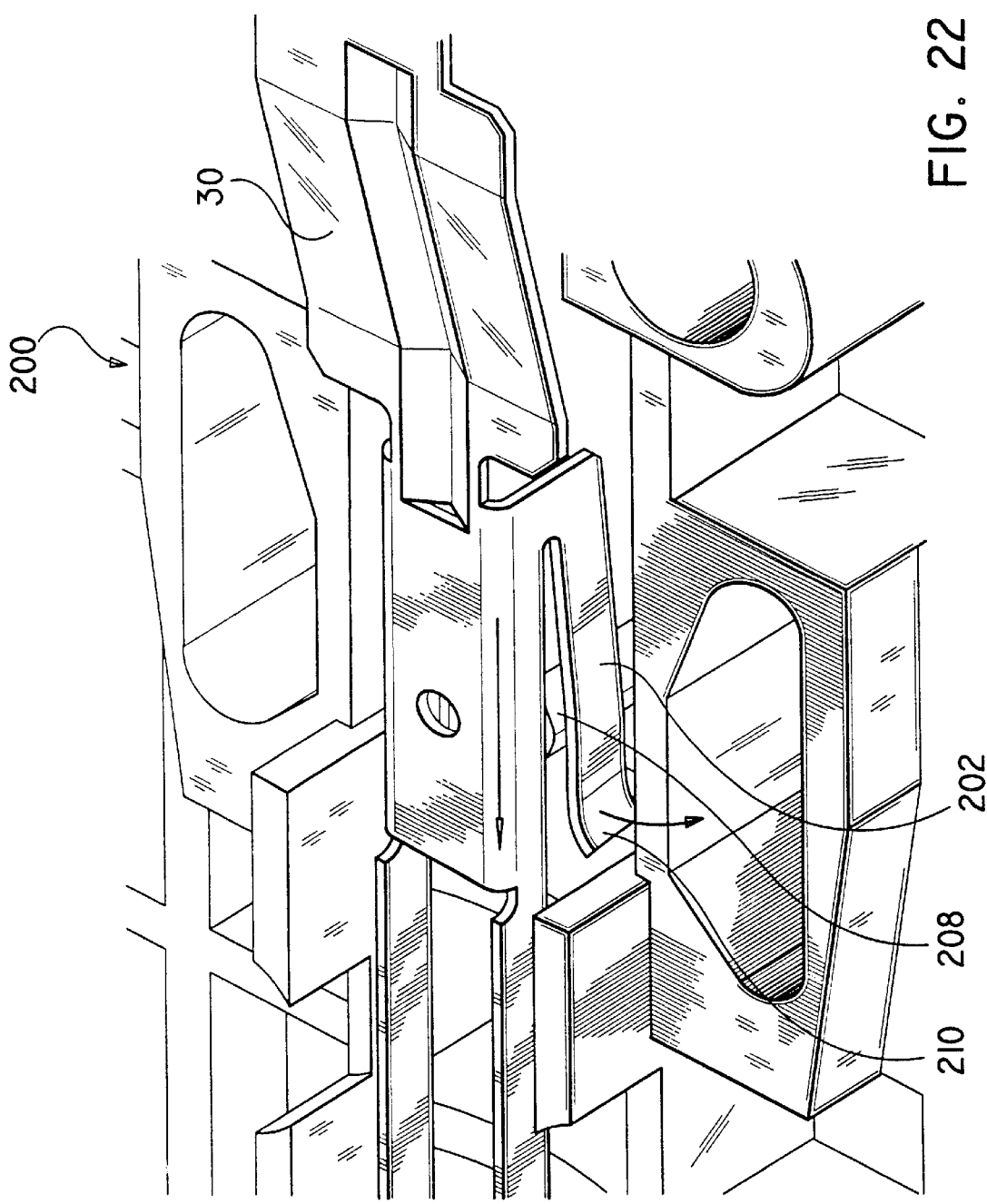
FIG. 22 illustrates the cam surfaces and spring members of the damping mechanism of FIG. 17 when the pusher bar is in the position of FIG. 20.

Referring now to FIGS. 20 and 21, as the handles fully open, post 104 has moved along the ramped surface of cam surface 108 to lift latch locking bar 110 over pusher bar latch tab 112. Due to the biasing of spring 46, pusher bar 30 moves in the distal direction until pusher bar drive tab 116 engages driving abutment surface 114 of drive plate 34 as shown in FIG. 21B. With reference to FIG. 22, pusher bar 30 accelerates under influence of spring 46 until the spring members 202, 204 of pusher bar 30 (and damping mechanism 200) engage cam surfaces 208 of cam boss 206. Flared ends 210 force spring members 202, 204 outwardly as shown, and the frictional engagement and resilient inward force of spring members 202, 204 against cam surfaces 208 causes a deceleration of pusher bar 30. The deceleration slows the pusher bar until pusher bar drive tab 116 engages driving abutment surface 114 of drive plate 34 to stop the distal movement of pusher bar 30.

As seen in FIG. 21, at this time cam plate 73 has returned to the at rest position, thus opening the jaw members 62 fully to accept the clip 26'. Once latch locking bar 110 has cleared pusher bar latch tab 112, pusher bar 30 is moved under the bias of spring 46 in the distal direction so that nose portion 118 slides the distalmost clip 26' into position between the jaws. At this point, the instrument is ready to apply another clip and is in the "ready" position.

Turning now to FIGS. 29–32, there is shown a first alternate embodiment of the damping mechanism which is provided in instrument 10. Damping mechanism 200 includes a clip spring 220 as shown in FIG. 29 which includes a resilient portion 222, a distal end 224, and proximal tab members 226 for securing the clip spring 222 to the inner wall of the channel cover 32. Clip spring 220 cooperates with detent 228 of pusher bar 30 (as shown in FIG. 30), and the resilient force of resilient portion 222 acts upon detent 228 to decelerate the distal advancement of pusher bar 30, in a manner similar to that as described above with respect to FIGS. 15–22.

Figure 23:
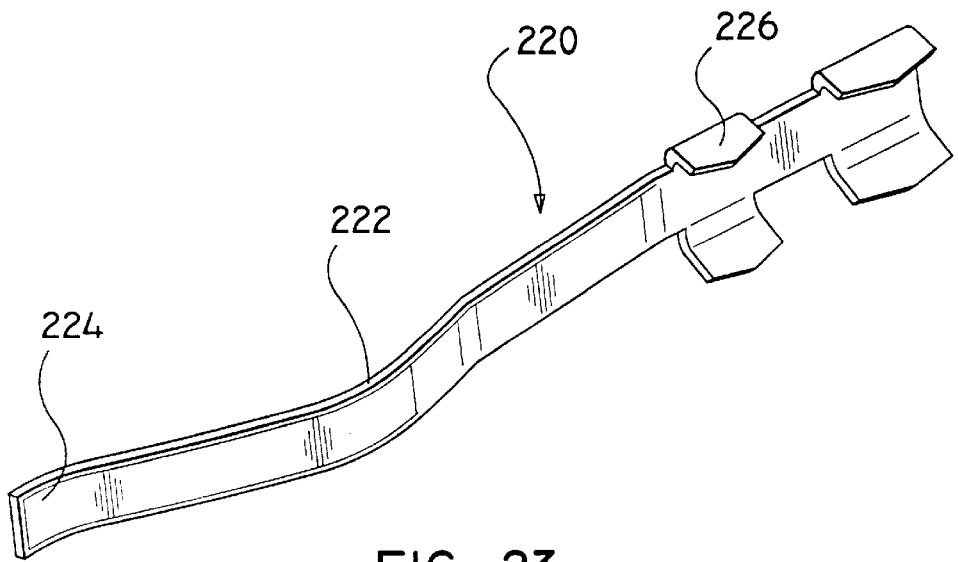
FIG. 23 illustrates an alternate spring member of the damping or braking mechanism of a second embodiment.
Figure 24:
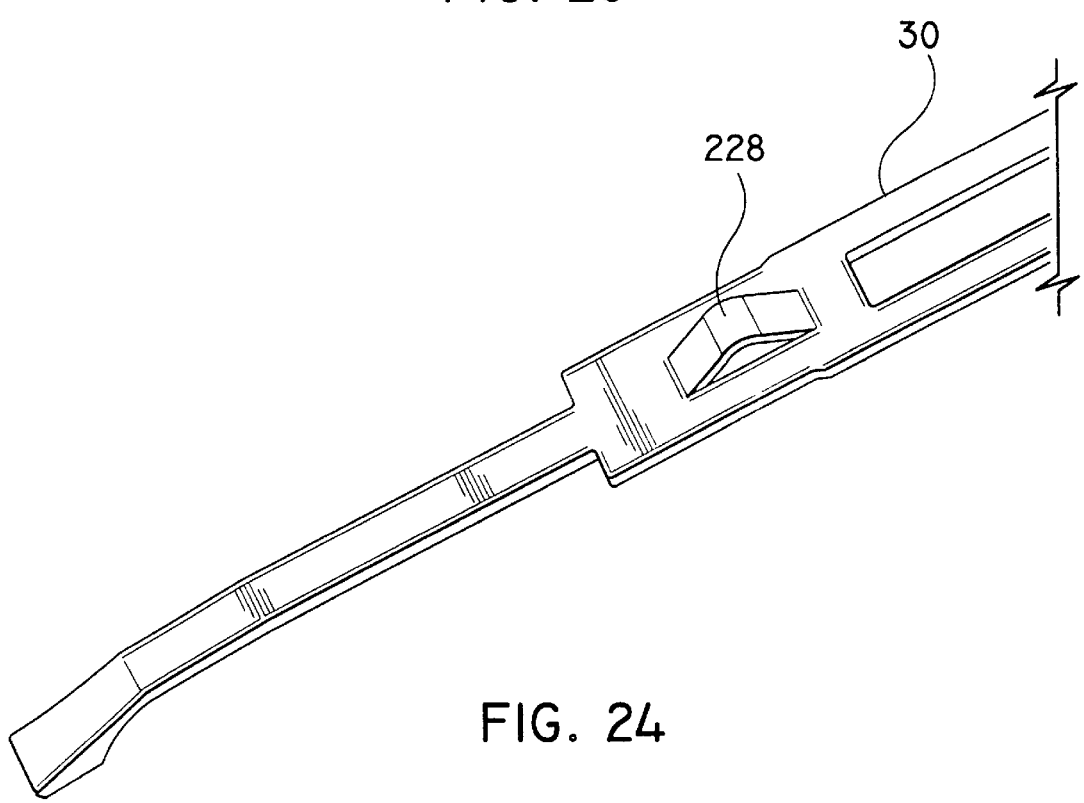
FIG. 24 illustrates an alternate cam surface, positioned on the pusher bar, of the damping or braking mechanism of FIG. 23.
Figure 25:
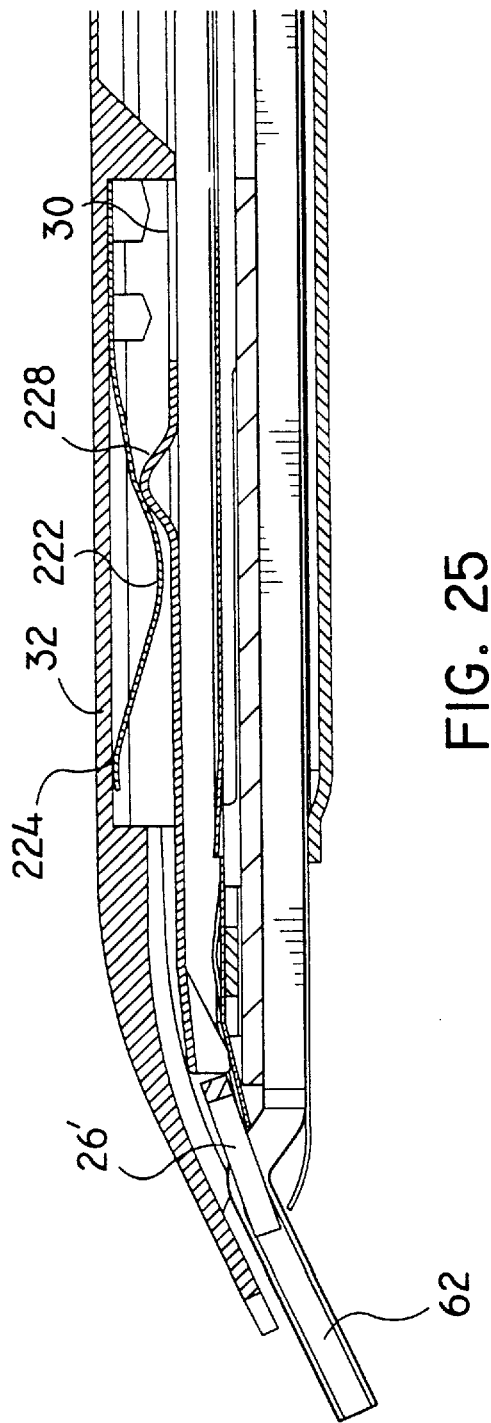
FIGS. 25 and 26 illustrate the damping or braking mechanism utilizing the components of FIGS. 23 and 24.
Figure 26:
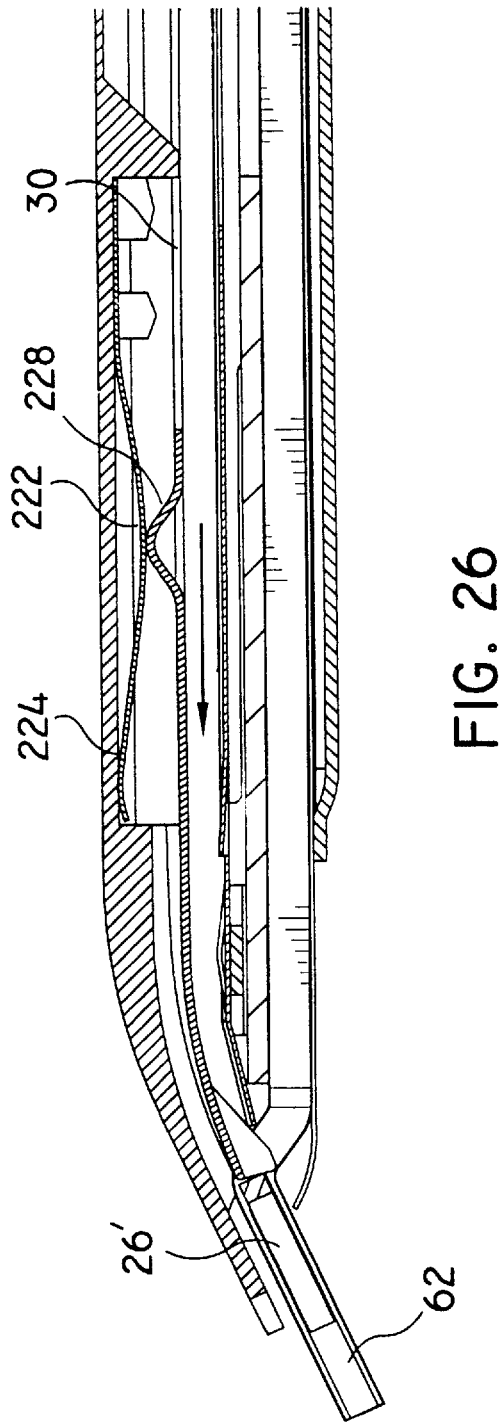

FIGS. 25 and 26 show the damping mechanism of FIGS. 23 and 24 in use. As the pusher bar 30 is released and advanced to position a clip between the jaw members, detent 228 moves distally under the influence of spring 46 until detent 228 engages resilient portion 222 of spring clip 220. The downward force (in relation to FIGS. 25 and 26) of resilient portion 222 against detent 228 decelerates pusher bar 30 and slows its distal advancement during feeding of a clip 26' to the jaw members 62. The clip is accurately placed in the jaw members as pusher bar 30 is slowed by the damping mechanism 200.

FIGS. 27–29 show a further alternate embodiment of the damping mechanism 200 of instrument 10. As seen in FIG. 27, pusher bar 30 is provided with a double spring clip damping portion 230, which includes a first spring clip 232 which extends in a proximal direction and a second spring clip 234 which extends in a distal direction. Spring clip 232 overlaps spring clip 234 as shown. In use, double spring clip damping mechanism 230 is positioned on pusher bar 30 within the handle portion 12 of instrument 10. As pusher bar 30 is released to position a clip between the jaws, pusher bar 30 accelerates in a distal direction until double spring clip mechanism 230 engages the proximalmost end of channel cover 32 within the handle portion 12. Spring clip 232 engages the inner surface of the channel cover 32, and is forced downwardly as shown in FIG. 29 against the biasing of second spring clip 234. The frictional engagement of the upper surface of spring clip 232 and the inner surface of channel cover 32, decelerates the forward advancement of pusher bar 30 to assist in accurately placing a clip between the jaw members 62.

While the clip applier has been particularly shown and described with reference to the preferred embodiments, it will be understood by those skilled in the art that various modifications and changes in form and detail may be made therein without departing from the scope and spirit of the novel aspects of the above-described clip applier. The damping mechanism may be provided in any clip applier, such as that shown, as well as endoscopic clip appliers and those having clip stacks instead of clip series. Accordingly, modifications such as those suggested above, but not limited thereto, are to be considered within the scope of what is considered to be the invention.

What is claimed is:

1. A surgical clip applier comprising:

a housing;

a pair of handles pivotably connected to opposite sides of said housing;

a body portion extending from said housing;

a plurality of clips;

a jaw assembly including a pair of jaw members extending from an end of said body portion opposite said housing, said jaw assembly adapted to accommodate a clip therein and being operable to effect closure of a clip in response to movement of at least one of the handles;

a clip pusher member slidably positioned in at least one of said body portion and said housing, said pusher member being operatively connected to at least one of said handles at a first end and having a nose portion terminating adjacent said jaw members at a second end, said pusher member being moved towards said housing as said handles are moved in a first direction to move said nose portion behind a distalmost clip in said plurality of clips, said pusher member being moved towards said jaw assembly as said handles are moved in a second direction to move said distalmost clip between said jaw members;

a resilient member connected to the pusher member for biasing the pusher member towards the jaw members; and a damping member for decelerating the advancement of the pusher member in the distal direction towards the jaw members.

2. A surgical clip applier according to claim 1, further comprising a latch mechanism in the housing for retaining the pusher member against the biasing of the resilient member, the latch mechanism including a releasing member to disengage the latch mechanism during movement of the handles in the second direction to permit advancement of the pusher member in the distal direction under influence of the resilient member.

3. A surgical clip applier according to claim 2, wherein the resilient member comprises a coiled spring.

4. A surgical clip applier according to claim 2, wherein the damping mechanism comprises at least one spring tab member to provide a force against the pusher member to counteract the acceleration force of the pusher member generated by the resilient member.

5. A surgical clip applier according to claim 2, wherein the damping mechanism comprises at least one spring tab member on the pusher member which cooperates with a portion of the housing to provide a force against the pusher member to decelerate the pusher member during distal advancement under the influence of the resilient member.

6. A surgical clip applier according to claim 2, wherein the damping mechanism comprises at least one spring tab member associated with the body portion which provides a force against the pusher member to decelerate the pusher member during distal advancement under the influence of the resilient member.

7. A surgical clip applier according to claim 5, wherein the spring tab member comprises a pair of spaced apart clip spring members which engage a cam boss on the housing, the cam boss causing deceleration of the pusher member by utilizing the resiliency of the clip spring members.

8. A surgical clip applier according to claim 5, wherein the spring tab member comprises a pair of overlapping, opposed spring blade members integral with the pusher member, the blade members engaging a portion of the housing to decelerate the pusher member by utilizing the resiliency of the blade members.

9. A surgical clip applier according to claim 6, wherein the pusher member includes a detent which engages the spring tab member to decelerate the pusher member by utilizing the resiliency of spring tab member.

10. In a surgical clip applier having a housing, at least one handle pivotably connected to the housing, a channel assembly extending from the housing, a series of clips carried by the channel assembly, a pair of jaw members extending from an end of the channel assembly opposite the housing, a clip follower for urging the series of clips towards the jaw members, a spring biased clip pusher member slidably disposed in the channel assembly for advancing a distalmost clip from the series of clips under the influence of the biasing spring to a position between the jaw members in response to movement of the handle, and a jaw closure mechanism to effect closure of the jaw members to deform a clip positioned therebetween in response to movement of the handle, the improvement which comprises:

a damping mechanism for decelerating the distal advancement of the pusher member, the damping mechanism creating a force on the pusher member to counteract an advancing force on the pusher member generated by the biasing spring.

11. The clip applier of claim 10, further comprising a latch mechanism for retaining the pusher member against distal advancement, and a release mechanism for disengaging the latch mechanism to permit distal advancement, the latch mechanism being engaged during a closing stroke of the handle and the release mechanism operating during an opening stroke of the handle.

12. The clip applier of claim 10, wherein the damping mechanism includes a pair of spring tab members positioned on the pusher member and a cam boss on the housing, the spring tab members engaging the cam boss during distal advancement of the pusher member to decelerate the pusher member by utilizing the resiliency of the spring tab members.

13. The clip applier of claim 10, wherein the damping mechanism includes at least one spring tab member positioned on the pusher member for engaging at least one of the housing and the channel assembly, the resiliency of the spring tab member generating a force on the pusher member to decelerate the pusher member during distal advancement.

14. The clip applier of claim 10, wherein the damping mechanism includes a spring clip member connected to the channel assembly and a detent positioned on the pusher member, the clip member and detent cooperating to generate a force on the pusher member to decelerate the pusher member during distal advancement.

15. The clip applier of claim 10, wherein the damping mechanism slows the pusher member as the pusher member feeds a clip into the jaws.

16. In a surgical clip applier having a housing, at least one handle pivotably connected to the housing, a channel assembly extending from the housing, a series of clips carried by the channel assembly, a pair of jaw members extending from an end of the channel assembly opposite the housing, a clip follower for urging the series of clips towards the jaw members, a spring biased clip pusher member slidably disposed in the channel assembly for advancing a distalmost clip from the series of clips under the influence of the biasing spring to a position between the jaw members in response to movement of the handle, and a jaw closure mechanism to effect closure of the jaw members to deform a clip positioned therebetween in response to movement of the handle, the improvement which comprises:

a damping mechanism operatively associated with the clip pusher member for retarding the distal advancement of the clip pusher member during advancement of a clip from the series to the jaw members, the damping mechanism applying a force on the clip pusher member to counteract a force on the clip pusher member generated by the biasing spring.

\* \* \* \* \*